US006455715B1

(12) United States Patent
Frische et al.

(10) Patent No.: US 6,455,715 B1
(45) Date of Patent: Sep. 24, 2002

(54) METHOD OF PRODUCING DICARBOXYLIC ACIDS SUITABLE FOR SYNTHESIS OF POLYMERS OR POLYAMIDES

(75) Inventors: Rainer Frische, Frankfurt am Main; Katja Hegwein, Reinhelm/Odenwald; Jürgen Volkheimer, Hanau, all of (DE)

(73) Assignee: Dr. Frische GmbH, Alzenau (DE)

( * ) Notice: Subject to any disclaimer, the term of this patent is extended or adjusted under 35 U.S.C. 154(b) by 0 days.

(21) Appl. No.: 10/032,515

(22) Filed: Oct. 24, 2001

Related U.S. Application Data

(62) Division of application No. 09/633,124, filed on Aug. 4, 2000, now Pat. No. 6,362,368.

(30) Foreign Application Priority Data

Aug. 5, 1999 (EP) ............................................. 99115528

(51) Int. Cl.⁷ ...................... C07C 231/00; C07C 233/00; C07C 235/00; C07C 237/00; C07C 229/00
(52) U.S. Cl. ........................ 554/112; 562/565; 562/590; 564/160; 564/216
(58) Field of Search ................... 554/37, 112; 562/565, 562/590; 564/160, 216

(56) References Cited

U.S. PATENT DOCUMENTS 2,813,113 A  11/1957  Goebel et al. ............... 260/406
3,402,108 A   9/1968  Oehlschlaeger et al. ...... 203/31

OTHER PUBLICATIONS

Pryde, et al., "Reaction of Azelaaldehydic Esters", *J. Amer. Oil Chemists' Society*, vol. 46, pp. 213–218, 1969.

Primary Examiner—Paul J. Killos
Assistant Examiner—Zachary C. Tucker
(74) Attorney, Agent, or Firm—Quarles & Brady LLP

(57) ABSTRACT

A method is described for producing saturated dicarboxylic acids with a chain length of C6 to C21 or the corresponding diamidic dicarboxylic acids from fatty acid cleavage of unsaturated fatty acids or the bis-fatty acid diamides of these unsaturated fatty acids by oxidative ozonolysis and subsequent separation and purification of the dicarboxylic acids, whereby after oxidative ozonolysis, the reaction products are dissolved at a high temperature in a carboxylic acid or a mixture of several carboxylic acids with a medium chain length of C6 to C12 or esters of short-chain alcohols of these carboxylic acids as the recrystallization solvent.

16 Claims, No Drawings

METHOD OF PRODUCING DICARBOXYLIC ACIDS SUITABLE FOR SYNTHESIS OF POLYMERS OR POLYAMIDES

CROSS-REFERENCE TO RELATED APPLICATIONS

This is a divisional patent application Ser. No. 09/633,124 field Aug. 4, 2000 of U.S. Pat. No. 6,362,368 granted Mar. 26, 2000 and entitled "Method of Producing Dicarboxylic Acids Suitable for Synthesis of Polymers or Polyamides" the disclosure of which is hereby incorporated by reference as if set forth in its entirety herein.

STATEMENT REGARDING FEDERALLY SPONSORED RESEARCH AND DEVELOPMENT

Not applicable.

BACKGROUND OF THE INVENTION

This invention relates to a method of producing dicarboxylic acids suitable for polymer or polyamide synthesis. The carboxylic acids comprise saturated dicarboxylic acids with a chain length of C6 to C21 produced by fatty acid cleavage of unsaturated fatty acids by means of oxidative ozonolysis and subsequent separation and purification of the dicarboxylic acids. Furthermore, the dicarboxlyic acids comprise diamidic saturated dicarboxylic acids in the form of bis-dicarboxylic acid diamides of saturated dicarboxylic acids with a chain length of C6 to C21 produced by cleavage of bis-fatty acids diamides of unsaturated fatty acids by oxidative ozonolysis and subsequent separation and purification of the diamidic dicarboxylic acids.

The fatty acid cleavage or splitting of unsaturated ative fatty acids to mono- and dicarboxylic acids which is used to produce dicarboxylic acids is known in general. The best known example of this in the relevant chemistry references is oxidative ozonolysis of oleic acid to pelargonic acid and azelaic acid. In oxidative ozonolysis, the unsaturated fatty acids are reacted with ozone to form ozonides, which are reacted directly, i.e., without isolating them, by oxidation to form the carboxylic acids. In this way, for example, oleic acid (C18:1-carboxylic acid) can be cleaved to form pelargonic acid (C9-monocarboxylic acid) and azelaic acid (C9-dicarboxylic acid).

In addition, it is also known that in the case of unsaturated native fatty acids, the two-step reaction described below is carried out to advantage in pelargonic acid as the solvent and in the presence of water. The weight ratios of fatty acid to solvent is approx. 1:1. The amount of water added depends on how the process heat is dissipated in the respective manner of managing the process. It is advantageous to use pelargonic acid because it is formed in the process anyway. Adding water prevents the formation of unwanted by-products in ozonolysis, but water also serves as a medium to absorb and dissipate the reaction heat in oxidation of the double bond of the fatty acid to the ozonide ring and oxidative cleavage of the latter to form carboxylic acids.

The reaction of monounsaturated fatty acids such as oleic acid with ozone as well as purification of the derivative products formed by oxidative ozonolysis, such as pelargonic acid and azelaic acid from oleic acid, have proven to be difficult. The main reasons include:

1. The reaction components used are not pure compounds such as pure oleic acid, but instead they are concentrates in which the component to be reacted is present in varying concentrations. In production technology, oleic acid is used in the form of a 70% to 80% concentrate (percent by weight of the type of monounsaturated oleic acid desired for the cleavage reaction, based on the total amount) containing saturated fatty acids as well as other monounsaturated fatty acids and polyunsaturated fatty acids.

2. Since oxidative ozonolysis breaks the starting compound down into two fragments, which are approximately equal in size in the case of oleic acid, the ratio of impurities to the desired substance changes to the detriment of the derivative compounds. For example, if 70% oleic acid concentrate contains 10 wt % saturated fatty acids and thus if the weight ratio of oleic acid to saturated fatty acids is 7:1, then after the reaction, the weight ratio of azelaic acid and pelargonic acid to saturated fatty acids is 3.5:1. This makes it difficult to isolate the pure derivatives in high yield.

3. As an extremely reactive oxidizing agent, ozone can also attack components of the reaction solution other than the desired reaction component(s). This is also true of the main component of the reaction solution which has already been converted to an ozonide according to this invention.

4. The reaction of ozone with double bonds involves a number of extremely unstable and reactive intermediates (see Organikum [Organic Chemistry], VEB Deutscher Verlag der Wissenschaften [People's Science Publishing House], eighth edition, 1968, page 252). These reactive intermediates can lead to unwanted by-products such as per acids, per esters and per ethers.

5. Polyunsaturated fatty acids react in oxidative ozonolysis to form short-chain mono- and dicarboxylic acids. This makes it difficult to isolate pure derivatives.

6. Polyunsaturated fatty acids contain active methylene groups which lead to unwanted side reactions, such as a shifting of the double bonds, cross-linking with other fatty acids and polymerization, especially after oxidative attack.

In industrial production technology, oxidative ozonolysis of unsaturated fatty acids is used mainly with oleic acid concentrate from tallow, with pelargonic acid serving as the reaction solvent, and mainly azelaic acid being formed as the dicarboxylic acid and pelargonic acid as the monocarboxylic acid. The unwanted by-products and derivatives can be minimized through a suitable choice of reaction conditions. Thus, oxidative ozonolysis of oleic acid concentrate is carried out in two steps, with the actual ozonolysis being performed at temperatures of less than 50° C. in a first reactor by addition of ozone onto the double bond with rearrangement to the ozonide ring. To prevent unwanted side reactions, the reaction heat is dissipated by means of intense heat exchange. Therefore, the reaction is carried out in the presence of water as the heat-absorbing and heat-dissipating medium. Then the oxidation of the ozonide ring with oxygen takes place at approximately 100° C. in a second reactor. The organic phase and the aqueous phase are brought in intense contact with the gaseous oxygen. Here again, the reaction heat released is dissipated by intense heat exchange with water to prevent unwanted side reactions.

With a two-step process, a yield of greater than 90% of the theoretical amount of pelargonic acid and azelaic acid is obtained, based on the starting oleic acid. A two-step oxidative ozonolysis with such yields is described, for example, in the article by Dr. Martin Witthaus of Henkel KGaA "Ozonolysis of unsaturated fatty acids" from the publication series of the Foundation of the Chemical Industry, no. 26, Frankfurt am Main, 1986.

The resulting products, in particular the resulting dicarboxylic acid azelaic acid, are obtained in complicated purification operations according to the state of the art. The pelargonic acid formed in the reaction and also used as a solvent can be recovered by distillation, with short-chain monocarboxylic acids being distilled over as the first runnings. In the case of oxidative ozonolysis of oleic acid concentrate, the resulting dicarboxylic acids can be obtained from the residue of pelargonic acid distillation by high-temperature vacuum distillation and/or by elution with water. The azelaic acid thus obtained is technically pure, but it still contains residues of monocarboxylic acids and other dicarboxylic acids, especially those with a shorter chain length.

To produce azelaic acid for polymer synthesis, the azelaic acid obtained in technical-grade purity must be further purified. For fine purification of the products, the respective mono- and dicarboxylic acid mixtures can also be subjected to fractional distillation, preferably after conversion to the methyl ester. Azelaic acid purified by this complicated procedure and having a dicarboxylic acids content of >99 wt % is converted to the diammonium salts of the corresponding diamines and condensed for the purpose of polyamide synthesis. Complicated purification processes of the type described here for azelaic acid can be found in U.S. Pat. No. 3,402,108, for example.

In oxidative ozonolysis of erucaic acid (C22:1), forming pelargonic acid and brassylic acid, brassylic acid (C13-dicarboxylic acid) cannot be obtained directly by distillation or eluted with water at a justifiable expense. The remaining traditional purification operations here include a time-consuming and tedious recrystallization from suitable solvents such as acetone, acetonitrile and ethanol/water and distillation of the esters (preferably the methyl ester) of the acid thus obtained.

Accordingly, it is customary in the related art to produce pure brassylic acid by the sequence of processes including 1. esterification of crude brassylic acid to methyl ester, 2. fractional vacuum distillation of the methyl ester and 3. saponification of the pure methyl ester. Since the methyl ester is used in many applications, synthesis of the pure acid can be omitted in these cases. Even the first purification step in this process chain involving synthesis of the ester and fractional vacuum distillation is associated with a great expense and a loss of yield.

The literature (see "Reactions of Azelaaldehydic Esters," by E. H. Pryde and J. C. Cowan, *J. Am. Oil Chem. Soc.*, volume 46, 1969, pages 213 to 218) describes ozonolysis of dioleodiamides and bis-oleic acid diamides such as those obtained by the reaction of diamines, such as ethylenediamine, with oleic acid. This process has not been carried out on an industrial scale. Bis-oleic acid diamide can be converted by oxidative ozonolysis to the respective diamidic dicarboxylic acid diazelaindiamide or bis-azelaic acid diamide, with the NH groups attached to the preferably long-chain structure, as described in the literature citation immediately above, for example. This dicarboxylic acid diamide is an interesting polymer building block, especially for synthesis of polyamides. It should be possible to convert bis-erucaic acid diamide to bis-brassylic acid diamide, which is also an interesting polymer building block, by a similar procedure.

However, the use of the diamidic dicarboxylic acid, namely bis-azelaic acid diamide, thus produced as a building block for high molecular polymers presupposes a very high purity. Therefore, according to the literature reference cited immediately above, an attempt was made to purify the filtrate of the reaction end product of oxidative ozonolysis which had cooled overnight by mixing it thoroughly and repeatedly with ether. The reaction product which was filtered and left to stand overnight also contained formic acid as a reaction solvent. However, according to the findings of the inventors of the present patent application, the melting range given in this literature reference for the bis-azelaic acid diamides thus obtained does not characterize building blocks of adequate purity for this purpose. For a sufficiently finely purified product, the melting range would have to be higher than that given there.

However, inadequate purification has some serious consequences. If such dicarboxylic acid diamides are synthesized from an oleic acid concentrate, mixed diamides such as stearo-oleodiamide are always formed in addition to the symmetrical dioleodiamides and can cleaved in oxidative ozonolysis to form mono-reactive diamide compounds. The latter lead to chain break-off in polymerization and thus cause a significant decline in overall properties of the resulting polymers if not removed adequately.

SUMMARY OF THE INVENTION

The object of the present invention is to provide a method that will make it possible in the simplest and least expensive manner to produce the desired saturated dicarboxylic acids suitable for synthesis of polymers or polyamides. Such dicarboxylic acids include "non-diamidic" dicarboxylic acid, such as those which can be obtained by oxidative ozonolysis of unsaturated fatty acids as well as "diamidic" dicarboxylic acids in form of bis-dicarboxlic acid diamides such as those obtained by oxidative ozonolysis of bis-fatty acid diamides of unsaturated fatty acids. The structure of these bis-dicarboxylic acid diamides which are still to be regarded as dicarboxylic acids because they still comprise acid groups, is as follows:

Bis[dicarboxylic acid]diamide:

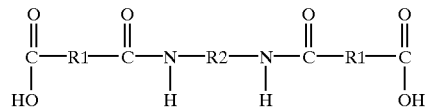

for example Bis[azelaic acid]ethylene diamide:

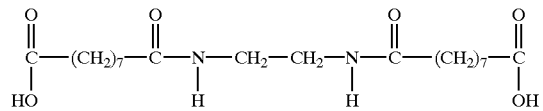

wherein the acid residue R1 is $(CH_2)_7$, and the amino residue R2 is $CH_2-CH_2$.

The principal structure can also be taken from the above cited document of Pryde and Cowan.

When dicarboxylic acids are mentioned below, these statements apply in general to both diamidic dicarboxylic acids and dicarboxylic acids that are non-diamidic.

The above object underlying the invention is solved by the method of the appended independent claims. Advantageous refinements of these methods are defined in the subordinate claims.

DETAILED DESCRIPTION OF THE INVENTION

The method according to said independent claims constitutes a departure from the prior art and its success is surprising in several regards.

The use of the carboxylic acids of a medium carbon chain length as defined in the claims, such as those corresponding to the chain length of the carboxylic acids obtained by oxidative ozonolysis of fatty acids, as recrystallization solvents and preferably also as wash solvents would represent an almost inconceivable measure to those skilled in the art.

Thus, those skilled in the art could not in principle expect recrystallization, regardless of the solvents used, to lead rapidly and unproblematically to products of the desired purity, because the properties of the impurities to be separated are too similar to those of the desired compound to be produced, and furthermore because, according to the previous findings and experience of the those skilled in the art, long-chain fatty acid derivatives tend to become included in the compounds crystallizing out. Therefore, experience indicated that recrystallization would have to be repeated several times, which would unavoidably lead to great losses of yield.

Thus, the procedure followed in the prior art has been to first remove by distillation the reaction solvent, usually in the form of the medium-length monocarboxylic acid (often pelargonic acid) which is formed in the reaction anyway, to simplify and thus facilitate the separation problem to be solved. This procedure is all the more self-evident as the pelargonic acid which is generally used as the reaction solvent is a monocarboxylic acid of the fatty acid type which has negative effects even in small amounts in most of the applications of dicarboxylic acids and in particular in synthesis of polymers. Then the dicarboxylic acid is purified by distillation, whereby residues of short-chain monocarboxylic acids and especially also pelargonic acid can be removed reliably. It would have to be surprising to those skilled in the art that adding pelargonic acid in particular or a carboxylic acid similar to it, in addition to the pelargonic acid not removed from the reaction end solution of oxidative ozonolysis, could simplify the separation problem and permit successful recrystallization. In this connection, the following circumstances and facts should be pointed out.

Easy-to-remove, low-molecular-weight compounds having pronounced chemical structural features that determine the dissolving properties are generally used as solvents for recrystallization. As a rule, conventional solvents with a graduated polarity are tested to find a suitable solvent. Examples of typical solvents include readily volatile hydrocarbons (extremely nonpolar), readily volatile aromatic hydrocarbons such as benzene and toluene, readily volatile, halogenated hydrocarbons such as chloroform and trichloroethylene, diethyl ether, acetone, ethyl acetate, alcohols such as methanol, ethanol, isopropanol, acetonitriles, organic acids such as formic acid and acetic acid and many others. These substances and especially mixtures usually include a solvent system that is suitable for solid-liquid separation (e.g., for recrystallization). The fatty acids or carboxylic acids and carboxylate esters of a medium chain length used according to this invention cannot be regarded as being similar to these conventional solvents typically used in the prior art. In comparison with such conventional solvents, the solvents of the present invention are not easy to evaporate nor is it readily apparent how they can otherwise be removed easily from the purified product. In addition, they do not have any apparent structural feature that would be especially suitable for the purification process to make them seem suitable for use for the purification process.

At the end of the oxidative ozonolysis process, the reaction products are usually present in a high concentration, dissolved in hot (approx. 100° C.) pelargonic acid. The dicarboxylic acids should crystallize out of such a solution on cooling—if at all—only in an extremely impure form with a large amount of included impurities. The latter can be expected in particular because dicarboxylic acids and impurities to be separated have similar structural features.

Therefore, after removing the mother liquor, only a very impure product should be obtained. The respective mother liquor should also contain substantial amounts of dicarboxylic acids in solution because of its relatively high concentration of impurities having a similar chemical structure. Separating the mother liquor should thus have resulted in great losses of yield.

However, the present inventors have surprisingly discovered that it is possible with the recrystallization solvents according to this invention to have pure dicarboxylic acids crystallize out in high yields. Furthermore, if the mother liquor adhering to the crystal sludge from recrystallization is then washed out with a cold wash solvent, it is also possible on the one hand a) to prevent a loss of yield due to the precipitated compound being redissolved, and, on the other hand, possible b) to prevent that impurities remain adhering to the dicarboxylic acid crystals when the mother liquor is removed.

It is surprising that the long-chain fatty acids such as palmitic acid and stearic acid, which are always present in the raw materials and have a very low solubility in the reaction solvent at cold temperatures, are not also precipitated at the same time. If the process starts with an oleic acid concentrate as the raw material having a stearic acid and palmitic acid content of 10 wt %, for example, and if an oleic acid concentrate/pelargonic acid weight ratio of 1:1 is used for the mixture, as is commonly used for ozonolysis, then a concentration is achieved after oxidative ozonolysis that, at a temperature less than 25° C., exceeds the solubility of the stearic acid and palmitic acid in the pelargonic acid solvent. Therefore, these acids should also precipitate out when the reaction solution is cooled to less than 25° C.

It is also difficult to separate the mother liquor from the solid pulp obtained after cooling the reaction solution through the usual separation operations such as filtration or centrifugation, because the filtration rate is low and decreases rapidly due to compaction of the solid mass, the pores of the filter material rapidly become clogged and considerable quantities of mother liquor remain in the solids. For those skilled in the art this usually indicates that, contrary to the findings of the present inventors, the precipitated solid phase is not a uniform product, but instead is a substance mixture, with the conclusion that the reaction solvent used cannot be suitable for purification of the desired substance by a solid-liquid separation method such as recrystallization.

According to this invention, carboxylic acids with a medium chain length of C6 to C12 or the esters of short-chain alcohols of these carboxylic acids are used as the recrystallization solvent. Such carboxylic acids are often used in the form of pelargonic acid as reaction solvents in oxidative ozonolysis of fatty acids. Furthermore, pleargonic acid is formed in the reaction. In these cases the pelargonic acid which is available anyway at the end of the reaction can be used as the reaction solvent according to this invention. Preferably an ester of pelargonic acid is also used and is added additionally. Thus, in the simplest case, the solution obtained at the end of oxidative ozonolysis, which is at a temperature of approximately 100° C., can be cooled to induce crystallization. If another reaction solvent which does not correspond to a carboxylic acid as defined in the appended claims is used for oxidative ozonolysis, such as chloroform (see the above-mentioned literature citation by Pryde and Cowan), the solvent can also be removed, however, and replaced by a recrystallization solvent according to this invention. Other suitable carboxylic acids in addition to pelargonic acid include hexanoic acid, heptanoic acid, etc. up to a chain length of C12.

The cooling temperature is preferably less than 25° C. However, in synthesis of diamidic dicarboxylic acid or bis-dicarboxlic acid diamides, it is also possible to use higher temperatures up to more than 40° C. at which the desired diamidic dicarboxylic acid can be crystallized out selectively in high yields. Since the process can be carried out easily, those skilled in the art can easily determine the optimum temperature at which the dicarboxylic acids can be crystallized out as thoroughly as possible, but the recrystallization solvent still contains the other reaction products of oxidative ozonolysis and other impurities in dissolved form and is not precipitated itself. Spectroscopic analysis of the ingredients of the mother liquor has proven a suitable method of control, where gas chromatographic analysis is performed on the esterified residues of the mother liquor.

The dicarboxylic acids that crystallize out are then obtained by separating them in the form of a crystal sludge when cool by filtering, decanting or centrifuging, but the crystal sludge still contains residues of the recrystallization solvent with the ingredients dissolved in it. The crystal sludge is optionally washed after additional recrystallization steps using a suitably cooled wash solvent or a wash solvent mixture, preferably again in the form of the medium length carboxylic acids or esters thereof, and then the wash solvent residues are removed by distillation or, as an alternative, by washing with acetone or hexane, for example. In this way, diamidic dicarboxylic acid as well as those that are no-diamidic can be obtained in high purity and good yield.

Oxidative ozonolysis preferably starts from monounsaturated fatty acids of native origin having a chain length of C14 to C24, e.g., oleic acid, erucaic acid, palmitic-oleic acid, myristic-oleic acid, eicosenoic acid or their diamides to obtain the highest possible yields. In principle, however, this method can also be carried out with polyunsaturated fatty acids. Oxidative ozonolysis is preferably carried out in the known two-step manner so that a yield of more than 85% of the theoretical is achieved, as in the state of the art. An example for oxidative ozonolysis as used in the present invention is e.g. given in Beilstein 2,I,290 and 2,II,603 (Syst.-Nr.178).

To dissolve the reaction products of oxidative ozonolysis, a temperature of no more than 100° C. is preferably used. This is not only advisable if the water of the reaction is left in the reaction product. If it is recalled that in the second step of the process of oxidative ozonolysis, a temperature of 100° C. is usually used anyway, and the by-products of the reaction that occur at this temperature must be removed, one should prevent any other problematical contaminants from forming due to higher temperatures used subsequently with the reaction product. Thus, decomposition products of the by-products already present may be formed at temperatures above 100° C., and their polymerization may also lead to other problematical contaminants that may also be difficult to remove.

Especially if further purification by formation of diammonium salt, as mentioned below, is omitted, the wash solvent residues are preferably removed only when the residues of recrystallization solvent adhering to the crystal sludge are essentially replaced by wash solvent by repeated addition of a certain quantity of wash solvent or by forcing a wash solvent column successively through the crystal sludge.

According to this invention, the above-mentioned medium length carboxylic acids (from C6 to C12, preferably with a chain length of C8 to C10, in particular with a chain length of C9) and their esters of short-chain alcohols (C1 to C6) such as the methyl, ethyl, propyl and isopropyl esters are preferably used as the recrystallization solvent for dicarboxylic acids with a chain length of C6 to C12, such as azelaic acid (C9) and brassylic acid (C13). Ozonolysis is performed, for example, with pelargonic acid as the reaction solvent and also so that the yield of dicarboxylic acid in ozonolysis and in oxidative cleavage of the ozonide ring amounts to at least 85 wt % of the yield to be expected theoretically. Measures are preferably also taken to ensure that no saturated fatty acids having a chain length of more than C28, preferably more than C26, are present, and that the amount of saturated fatty acids having chain lengths greater than C14 and smaller than C26 is less than 15 wt %, preferably less than 10 wt %, in the starting mixture of the fatty acid mixtures to be subjected to ozonolysis. If fatty acid diamide mixtures are used instead of fatty acid mixtures in oxidative ozonolysis, this means that the saturated fatty acids bound in the fatty acid diamides should constitute less than 15 wt %, preferably less than 10 wt % of the total amount of the fatty acids. In the case of dicarboxylic acids that are non-diamidic, the recrystallization solvent is preferably used with one to ten times the amount of dicarboxylic acids, monocarboxylic acids such as stearic acid and by-products of oxidative ozonolysis which remain after removal of the pelargonic acid reaction solvent. If working with diamidic dicarboxylic acids as the end product of oxidative ozonolysis, it is advisable instead to add the recrystallization solvent with two to fifteen times the weight amount of the remaining reaction end product minus said reaction solvent. Moreover, the upper limit for this addition must be defined from the standpoint of yield and ease of handling. It is possible in principle to work with larger amounts.

Furthermore, the products are preferably crystallized out of a solution that is saturated at approximately 80° C. in the case of non-diamidic dicarboxylic acids (and are crystallized out of a solution that is saturated at approximately 100° C. in the case of diamidic dicarboxylic acids) by cooling to temperatures below 25° C., preferably to approximately 15° C., and the crystal sludge which is separated is freed of as much of the adhering mother liquor as possible. The latter is performed by washing with cold solvent (below ambient temperature, for example less than 25° C., preferably approximately 15° C.), with the respective cooling temperature being essentially retained. The washing may be performed with fatty acids and fatty acid mixtures of fatty acid esters and fatty acid ester mixtures as well as mixtures of acids and esters of the chain lengths indicated above for the recrystallization solvent. When using esters, the lower temperature limit may also be reduced because they have lower melting points.

After removal of the wash solvent residues remaining in the solids treated according to this invention, such as pelargonic acid and/or pelargonic acid methyl ester, preferably by distillation, the dicarboxylic acids such as azelaic acid and brassylic acid remain in high purity. Long-chain monocarboxylic acids such as palmitic acid and stearic acid as well as unwanted by-products of ozonolysis are separated with the wash water or mother liquor. When using mixtures of solvent acids and/or esters, the solvent can be recovered by distillation and used further without being separated into individual components.

The simplest method (from the standpoint of production technology) of removing the fatty acids and fatty acid esters used as wash solvents is to remove them by distillation, but small amounts (1 wt % to max. 2 wt %) wash solvent generally remain in the purified product. These residues are insignificant for most applications, but not when using the purified products for production of polymers.

Separation of residues of these wash solvents and thus fine purification of the dicarboxylic acids can surprisingly be performed simply by converting the dicarboxylic acids to solid diammonium dicarboxylic acid salts, preferably in an alcoholic solution at the isoelectric point (pH approx. 7.5). A conversion to solid diammonium dicarboxylic acid salts is quite common in polyamide synthesis. Purification is possible with no problem even when the solvent residue content in the crystal sludge is significantly more than 2 wt % up to 50 wt %. This is all the more surprising since inclusion in the precipitated salts would be expected in particular because of the similar chain lengths. However, the ammonium salts of the residues of the wash solvent fatty acids as well as the residues of the wash solvent esters remain in the alcoholic mother liquor. The mother liquor adhering to the crystal sludge can be removed completely without any mentionable losses by washing with alcohol. The resulting diammonium salts can be used to advantage directly for polyamide synthesis.

In addition, entrained residues of the original impurities e.g. long-chain saturated fatty acids, fatty acid esters, ethers, etc., such as those which may remain with inadequate washing of the starting solid mass according to the appended independent claims can also be successively removed when the dicarboxylic acids are purified by way of the diammonium salts. This yields additional production reliability and can even be used to advantage by premature termination of the washing step and wash solvent removal step according to the appended independent claims if the final purification is to be performed by way of the diammonium salt. This makes it possible to greatly reduce the cost of the purification operations. The diamines are thus an aid to purification of the non-diamidic dicarboxylic acids in particular as well as being a reaction component to produce the starting components for polyamide synthesis. If they are used as an aid, they can be recovered and reused in the known manner. In principle, however, purification of the diamidic dicarboxylic acids can also be performed by forming the salt, as explained in greater detail below.

The distillation bottoms remaining after distillative recovery of the solvents still contain residues of dicarboxylic acids. These can also be recovered if the distillation bottom product is dissolved in alcohol and the dicarboxylic acids are precipitated as diammonium salts.

The lost yield can be minimized by combining the two purification operations described above, namely washing the dicarboxylic acid solids precipitated from the reaction solvent and precipitating the dicarboxylic acid as a diammonium salt.

This subsequent salt-forming step can be carried out directly following process step c1) of the appended independent claims according to the subclaims and Example 4, omitting steps c2) and c3), or after using water as the wash solvent in process steps c2) and c3) for an acid (such as formic acid) used in the oxidation step. In this case, however, considerable quantities of pelargonic acid are usually still present in the filter cake (up to 50 wt %, as mentioned above) and large amounts of amides accordingly are needed for salt formation. Therefore, salt formation preferably takes place only after washing the crystal sludge according to step c2) following the process step c3), preferably using the wash solvent characterized according to the subclaims.

Mixtures of dicarboxylic acids such as those obtained by oxidative ozonolysis of unsaturated native fatty acids with different double bond positions, can surprisingly be obtained as pure dicarboxylic acid mixtures (non-diamidic) with chain lengths of more than C6 up to C21, freed of monocarboxylic acids and other impurities formed by ozonolysis. Thus, a mixture of azelaic acid and brassylic acid which is free of monocarboxylic acids and unwanted by-products of oxidative ozonolysis is obtained from the fatty acid mixtures obtained by saponification of eruca-rich rapeseed oil or Crambe seed oil, so that the dicarboxylic acid mixture can be used directly for conversion to polyamides. The resulting dicarboxylic acid mixtures can be separated into the pure individual components by known methods. The same holds true for the mixed-composition diamides of the corresponding unsaturated fatty acids after oxidative ozonolysis performed to form dicarboxylic acid diamides the so-called diamidic dicarboxylic acids.

In particular, fatty acid mixtures are suitable for use as a raw material for production of dicarboxylic acid mixtures such as those obtained by saponification of oils, in particular high-oleic oils and fish oils, freed of polyunsaturated fatty acids by partial hydrogenation. Because of the partial hydrogenation and the resulting shift in double bonds, an entire spectrum of dicarboxylic acids of different chain lengths (from C6 to C12) is obtained. Again in this case, by using the method described here, the dicarboxylic acid mixture can be freed of non-dicarboxylic acid products such as monocarboxylic acids and by-products of ozonolysis that would interfere with polyamide synthesis.

This invention thus makes it possible to obtain pure dicarboxylic acids and dicarboxylic acid mixtures by ozonolysis in a much simpler method than that according to the state of the art.

It has surprisingly also been found that the types of dicarboxylic acid diamides, or better yet, diamidic dicarboxylic acids that are of interest for polymer synthesis and are described in the literature reference "Reactions of Azelaaldehydic Esters" cited above can also be obtained similarly in high yields and in high purity by the method of the present invention. The following procedure is preferably used here. Ozonolysis of the diamides of the fatty acids is performed here in carboxylic acids with a chain length of C7 to C12, preferably (pelargonic acid) C9 as the reaction solvent, where no clear solution need be present. A stirrable reaction mass is ensured by using a suitable amount of solvent and a suitable temperature. The reaction is therefore carried out with thermostatic control at elevated temperatures of approximately 60° C. to 80° C. in the presence of water before the second step of the two-step oxidative ozonolysis takes place.

The reaction products of oxidative ozonolysis are dissolved completely in the reaction solvent after heating to 100° C. and then are crystallized by cooling, separated from the reaction solvent and washed with the cold wash solvents mentioned above.

The adhering wash solvent is largely removed by distillation, for example, and by using alcohol as the solvent, the residue is converted to salts of diamines that are used for polymer synthesis. These preferably include linear hydrocarbon chains with a chain length of C4 to C22 containing terminal amino groups.

Monocarboxylic acids and the by-products formed by ozonolysis can be mostly removed in the first crystallization step in this way. In the following step of converting the dicarboxylic acids to the ammonium salts of diamines, the diamidic dicarboxylic acids can be crystallized out as ammonium salts through a suitable choice of the reaction solvent, while the residues of monocarboxylic acids still present will remain in solution. As already shown, the same holds true for the carboxylic acids that are non-diamidic and are to be purified by forming the salt. For this reason, the criteria for salt formation explained below are the same for both cases, namely for purification of carboxylic acids that are non-diamidic by means of salt formation and for forming salts of the diamidic carboxylic acids for polyamide synthesis.

Water-soluble alcohols or alcohol mixtures (methanol, ethanol and propanols) have proven suitable as reaction solvents for forming the salts and are preferably added in five to ten times the amount by weight to the stoichiometric amount of dicarboxylic acid and diamine.

By adding small amounts of water, the solubility of the salt can be influenced so that only the dicarboxylic acids or the diamidic dicarboxylic acids crystallize as salts out of a hot, clear solution when cooled. The salts can be washed with corresponding cold mixtures of alcohol and water and thus freed of adhering mother liquor.

The solubility of the salt can also be influenced through the choice of the salt-forming diamine. Thus, the salts of azelaic acid and short-chain diamines have a relatively good solubility, whereas the salts formed with longer-chain diamines have a lower solubility.

The salts of the diamidic dicarboxylic acids thus formed can be used directly for polyamide synthesis, optionally after recrystallization in alcohol from the corresponding alcohol-water mixtures and drying.

The dicarboxylic acids can also be released with dilute mineral acids in the usual way, freed of diammonium salt of mineral acids thus formed by washing and obtained in pure form. The corresponding diamines can in turn be recovered by neutralizing the mineral acids in a known way.

The diammonium salt synthesis can take place as follows:

The reaction products of oxidative ozonolysis with diamidic dicarboxylic acid or non-amidic dicarboxylic acid are dissolved in the reaction solvent by heating, the hot solution is optionally washed with hot water, the organic solution freed of wash water is precipitated and separated by filtration. The resulting solid residue containing pelargonic acid is mixed, preferably after washing, with an approximately stoichiometric amount of the corresponding diamine, then this mixture is heated to the boiling point with a five-fold to ten-fold amount of absolute alcohol by weight and, if a clear solution is not then obtained, enough water is added at the boiling point until a clear solution is obtained. An exact stoichiometric addition is not required because of the subsequent pH adjustment. The pH of the clear solution is adjusted to approximately 7.5 by adding either crude dicarboxylic acid or diamidic dicarboxylic acid, and the solution is cooled to room temperature.

The present invention will be explained in greater detail below on the basis of preferred examples. For all the examples, oxidative ozonolysis of the acids or their diamides was performed as a two-step process in the known way with yields of more than 85%. The yield was calculated on the basis of the aliquots analyzed and the results were checked.

Oxidative Ozonolysis for the Starting Material

I. Erucaic Acid to Pelargonic Acid and Brassylic Acid (Examples 1 through 3)

100 g erucaic acid (average composition: 91.5 wt % C22:1, 1.5 wt % C22:2, 0.4 wt % C18:1, 0.4 wt % C18:2, 6 wt % saturated long-chain fatty acids) was ozonized and subsequently oxidized using 100 g pelargonic acid as the reaction solvent and water as an aid in the usual way well known in the art. For the oxidation step, formic acid with hydrogen peroxide was used. According to the theory, the reaction solvent should contain the following:

67.1 g brassylic acid formed in the reaction (with very little of other dicarboxylic acids)

43.8 g pelargonic acid formed in the reaction (with very little medium chain length monocarboxylic acids)

6.0 g unconverted saturated long-chain fatty acids of the starting raw material.

After the oxidation step, the oxidation product was present in solution in a hot (100° C.) clear organic phase (pelargonic acid with formic acid dissolved in it and water). The reaction mixture was cooled to 20° C. The top phase solidified completely to form a white crystal sludge cake. The aqueous phase was separated and discarded. The crystal sludge cake was stirred and the resulting sludge was washed twice with cold water at 20° C. and filtered sharply with suction using a Büchner funnel and a black band filter. The resulting filtrates from washing, each having a clear aqueous bottom phase and a clear reaction solvent top phase (pelargonic acid) were collected and combined. The remaining filter cake was

EXAMPLE 1

1. Analysis of the Residue in the Reaction Solvent Separated

An aliquot (7 g) of the mother liquor, i.e., the reaction solvent top phase, was freed of volatile components by distillation in vacuo, with 5.95 g pelargonic acid distilling over and 0.65 g non-volatile components remaining. The gas chromatogram of the non-volatile components converted to methyl esters showed 30% brassylic acid methyl ester and 70% fatty acid ester. The gas chromatogram was obtained with a gaschromatographic device GC 8160 produced by Fisons.

Interpretation:

Based on the total batch, the reaction solvent phase contains (0.65/5.95)(100+43.8) g=15.7 g non-volatile residue in solution. It contains long-chain, saturated fatty acids, by-products and unprecipitated brassylic acid (approximately 4.5 g according to the gas chromatogram).

2. Analysis of the Crude Brassylic Acid from the Filter Cake of the Cold Reaction Solvent An aliquot (8.5 g) of the filter cake was freed of volatile components by distillation in vacuo. 3.7 g pelargonic acid distilled over (with a very small amount of other medium-length monocarboxylic acids), leaving a residue of 3.9 g (referred to below as crude brassylic acid).

The residue had a melting range of 107.5° C. to 109.6° C. (the lowest fusion point (Fp) of pure brassylic acid found in the literature was 112° C. to 113° C.). Neutralization titration of the residue showed a deviation of approximately 0.5% in comparison with pure brassylic acid.

EXAMPLE 2

An aliquot (20 g) of the filter cake washed with water and filtered sharply with suction was stirred once thoroughly with 45 g cold pelargonic acid at 15° C. and filtered sharply with suction, yielding 12 g filter cake and 48 g mother liquor.

1. Analysis of the Mother Liquor

An aliquot (7 g) of the mother liquor was freed of volatile components by distillation in vacuo, leaving 0.2 g non-volatile components. The gas chromatogram of the non-volatile components reacted to form methyl esters showed the same composition as the residue of the first mother liquor.

2. Analysis of the Purified Brassylic Acid from the Filter Cake of the Cold Pelargonic Acid An aliquot (6.4 g) of the filter cake washed with pelargonic acid water was freed of volatile components by distillation in vacuo, with 2.21 g pelargonic acid distilling over, leaving 3.6 g residue. The residue (purified brassylic acid) had a melting range of 110.5° C. to 112° C. (melting point of pure brassylic acid according to the literature: 112° C. to 113° C.). Neutralization titration of the residue yielded a deviation of <0.5% in comparison with pure brassylic acid.

Interpretation:

There is no redissolving of the brassylic acid by cold washing. Only mother liquor residues with the substances contained dissolved in the mother liquor are diluted and washed out. By washing once, the brassylic acid was obtained in practically pure form.

EXAMPLE 3

Purification of Crude Brassylic Acid by Way of the Hexamethylenediammonium Salt 12.4 g crude brassylic acid synthesized according to Example 1 and containing residues of pelargonic acid was dissolved in 20 g technical-grade ethanol (5% water content by weight) at a high temperature (solution 1). In parallel with that, 5.5 g hexamethylenediamine was dissolved in 20 g technical-grade ethanol (solution 2). While stirring, solution 2 was added to solution 1 at a high temperature (approximately 70° C.) until the pH of the mixture was 7.5. The mixture was cooled to room temperature. The resulting solid crystal sludge was stirred and separated from the mother liquor as thoroughly as possible by filtration.

22 g yellow mother liquor was obtained; after removing the ethanol, 0.54 g waxy mass remained as a residue. The thin-layer chromatogram prepared in this case showed several impurities in addition to brassylic acid.

The remaining crystal mass which was largely freed of mother liquor by filtration was stirred with 40 g hot ethanol, then cooled, freed of most of the washing ethanol by filtration and then dried, yielding 16.5 g white powder. The thin-layer chromatogram showed brassylic acid without any pelargonic acid. The washing ethanol (approximately 40 g) contained 0.45 g waxy residue. The thin-layer chromatogram contained several impurities in addition to brassylic acid.

It should be pointed out that before preparing the respective thin-layer chromatograms for detection of brassylic acid, the salt thus obtained was converted back to the acid form by acidifying with diluted sulphuric acid.

Interpretation:

This experiment shows that the by-products present in crude brassylic acid after oxidative ozonolysis as well as residues of the reaction solvent pelargonic acid can be separated by way of the diammonium salt without any mentionable losses.

II. Oxidative Ozonolysis for the Starting Material of Example 4

Bis-eruca-ethylenediamide to Bis-brassylic Acid Ethylenediamide and Pelargonic Acid The reaction was performed with bis-eruca-ethylenediamide as the raw material by analogy with oxidative ozonolysis, but in this case the ozonolysis was performed in pelargonic acid at an elevated temperature of approximately 60° C. After cooling the hot oxidation product and washing twice with water, the mixture was filtered as described in I, supra, and the remaining filter cake was obtained.

EXAMPLE 4

Purification of Bis-brassylic Acid Ethylenediamide Containing Pelargonic Acid by Way of the Ethylenediammonium Salt 15.7 g of the filter cake from II containing pelargonic acid (50 wt %) and bis-brassylic acid ethylenediamide from the reaction was reacted with 3.6 g hexamethylenediamine in 450 mL ethanol, and 7.5 g of the diammonium salt of bis-brassylic acid ethylenediamide precipitated out. Only traces of pelargonic acid were present in the salt according to the thin-layer chromatogram. The residue of the mother liquor (10.9 g) contained pelargonic acid (as the salt) and impurities.

III. Oxidative Ozonolysis for the Starting Material of Example 5

Oleic Acid to Azelaic Acid and Pelargonic Acid

This reaction was carried out by analogy with the oxidative ozonolysis described under I, supra, except that the raw material used was high-oleic sunflower acid (90 wt % oleic acid, 3 wt % linoleic acid, 6 wt % palmitic and stearic acid, and 1 wt % fatty acids with chain lengths >C20). A mixture of ozone and oxygen was introduced and the temperature was held at about 40° C. to about 50° C. As soon as double-bonds could not be detected any more which was proved by well known Bromine-Test, the introduction of ozone was stopped. Subsequently, oxygen was introduced at 100° C. until aldehydes could not be detected any more.

After cooling the hot oxidation product to 40° C., the aqueous phase (bottom phase) was separated and discarded. The organic top phase (pelargonic acid phase) was cooled and solidified to a crystal sludge, which was filtered as described in I and the remaining filter cake was obtained.

EXAMPLE 5

The filter cake from III was treated with cold water (approximately 20° C.) as in I and filtered, leaving a filter cake containing pelargonic acid (79.2 g). This filter cake was the starting material for purification operations 1 through 4.

1. Crude Azelaic Acid

An aliquot (8.1 g) of the filter cake thus obtained was subjected to distillation in vacuo to remove the pelargonic acid and volatile compounds. There remained a residue (crude azelaic acid, 4.23 g) which was solid at low temperatures.

Neutralization titration to determine the azelaic acid content showed that consumption of NaOH was reduced by 3.9% in comparison with consumption of NaOH when working with pure azelaic acid. For titration, the azelaic acid was dissolved in ethanol. The titration was performed with 1 N NaOH and phenolphthalein.

2. Azelaic Acid Washed with Cold Pelargonic Acid

An aliquot (15 g) of the filter cake was stirred thoroughly with cold (approximately 20° C.) pelargonic acid (35 g) and then filtered through a Büchner funnel.

An aliquot (8.1 g) of the filter cake thus obtained was subjected to distillation in vacuo to remove the pelargonic acid and volatile compounds. There remained a residue (purified azelaic acid, 3.54 g) which solidified when cooled.

Neutralization titration to determine the azelaic acid content showed that consumption of NaOH was reduced by 0.77% to 0.8% in comparison with that using pure azelaic acid.

3. Azelaic Acid Recrystallized from Pelargonic Acid

An aliquot (15 g) of the filter cake was dissolved hot in pelargonic acid (40 g), then cooled to room temperature again, and the precipitated crystals were filtered through a Büchner funnel, leaving 14.8 g filter cake moistened with pelargonic acid.

An aliquot (6.97 g) of the filter cake obtained in this way was subjected to distillation in vacuo to remove the pelargonic acid and low-boiling compounds. There remained a residue (purified azelaic acid 2.23 g) that was solid at low temperatures.

Neutralization titration to determine the azelaic acid content showed a 0.9% reduced consumption of NaOH in comparison with using pure azelaic acid.

A comparison of experiments 2 and 3 shows that the first recrystallization in pelargonic acid of oxidative ozonolysis with a subsequent washing operation according to experiment 2 yields a very good purity.

4. Azelaic Acid Washed with Cold Pelargonic Acid and then Recrystallized from Pelargonic Acid, Condensation with Hexamethylenediamine to Polyamide The remaining residue of the wet filter cake containing pelargonic acid was washed with cold pelargonic acid as described in 2. The resulting filter cake was combined with fractions 1 through 3 (filter cake residues and solid residues) containing azelaic acid. The total amount was recrystallized from pelargonic acid (120 g) and filtered. The filter cake was subjected to distillation in vacuo to remove the pelargonic acid and volatile compounds.

Neutralization titration to determine the azelaic acid content did not show any greater or lesser consumption of NaOH in comparison with pure azelaic acid. The resulting product was condensed to polyamide with hexamethylendiamine in an autoclave (100 ml autoclave A86/1 of Roth, Karlsruhe) in a known way (final condensation temperature approximately 300° C.).

The resulting polyamide had the expected properties: it was colorless, slightly opalescent, viscous at room temperature and not crumbly, capable of cold drawing, having an extremely high tensile strength and suitable for thermoplastic processing.

EXAMPLE 6

Purification of Brassylic Acid and Azelaic Acid from Oxidative Ozonolysis of Erucaic Acid/oleic Acid Mixtures (Fatty Acids of Crambe Oil, "Crambe Acid")

The reaction was performed like oxidative ozonolysis, as described in I, except that crambe acid (13 wt % oleic acid, 8 wt % linoleic acid, 6 wt % linolenic acid, 62 wt % erucaic acid and 3 wt % palmitic and stearic acid and 8 wt % fatty acids with chain lengths of more than C20 was used as the raw material.

After cooling the hot oxidation product to room temperature (approximately 20° C.), the resulting crystal sludge was filtered as described in I and the remaining filter cake was obtained. It was washed with water as described in I and filtered, and a filter cake was obtained by filtration. The filter cake was freed of pelargonic acid and volatile compounds by distillation in vacuo, yielding a distillate (28.3 g pelargonic acid) and a residue (37.7 g crude dicarboxylic acid mixture) that was solid at room temperature. The latter was the starting material for the following tests.

1. Crude Dicarboxylic Acids

An aliquot of the crude dicarboxylic acids was esterified to methyl esters with acid catalysis in a known way. For this purpose, the crude dicarboxylic acid was heated in methanol together with paratoluol-sulfonic acid for five hours.

The gas chromatography spectrum showed as main peaks azelaic acid dimethyl ester and brassylic acid dimethyl ester in the expected ratio of the integration areas of their signals of approximately 1 to 4. In addition, impurities such as the methyl esters of palmitic acid, stearic acid and eicosenoic acid could be seen clearly, constituting approximately 10% of the total integration area of the signals.

2. Recrystallization from Pelargonic Acid

The remaining main quantity of the crude dicarboxylic acid (approximately 35 g) was recrystallized from pelargonic acid (200 mL) and the crystal mass was filtered out. The filter cake was freed of pelargonic acid by distillation in vacuo, yielding 26.4 g solids (purified dicarboxylic acid mixture). An aliquot of the dicarboxylic acids thus purified was esterified with acid catalysis to form methyl esters in a known way. The gas chromatography spectrum of the methyl esters showed as main peaks azelaic acid dimethyl ester and brassylic acid dimethyl ester. The integration part of the signals of palmitic, stearic and eicosenoic acid methyl ester had decreased significantly (by a factor of approximately 10) in comparison with the spectrum of the methyl esters of the crude dicarboxylic acid mixtures.

We claim:

1. A method of producing diamidic saturated dicarboxylic acids in the form of bis-dicarboxylic acid diamides of saturated dicarboxylic acids with a chain length of C6 to C21 from cleavage of bis-fatty acids diamides of unsaturated fatty acids by oxidative ozonolysis and subsequent separation and purification of the dicarboxylic acid diamides, said method comprising the steps of:
    a) after having carried out oxidative ozonolysis, dissolving the reaction products of oxidative ozonolysis under heating in a recrystallization solvent selected from a group consisting of carboxylic acids of a chain length of C6 to C12, a mixture of several of said carboxylic acids, and esters of short-chain alcohols of said carboxylic acids,
    b) cooling the solution to a temperature at which the diamidic dicarboxylic acid crystallize out, but the recrystallization solvent still contains the other reaction products of oxidative ozonolysis and other impurities in dissolved form and does not precipitate itself, and then
    c) obtaining the crystallized diamidic dicarboxylic acid by
       c1) separating them while still cool in the form of a crystal sludge which still contains residues of the recrystallization solvent with the dissolved components in it,
       c2) washing the crystal sludge with a below ambient temperature wash solvent or a wash solvent mixture, optionally after additional recrystallization steps, and
       c3) subsequently removing the wash solvent residues.
2. The method according to claim 1, wherein the bis-fatty acid diamides which are subjected to cleavage are derived from unsaturated fatty acids which are one of fatty acids or fatty acid mixtures of native origin with a chain length of C14 to C24.
3. The method according to claim 2, wherein the unsaturated fatty acids are high-oleic oils of native origin.
4. The method according to claim 1, wherein a monocarboxylic acid obtained in the oxidative ozonolysis is used as the recrystallization solvent to dissolve the other reaction products of ozonolysis.

5. The method according to claim 4, wherein the monocarboxylic acid is pelargonic acid.

6. The method according to claim 4, wherein the recrystallization is conducted at no more than 100° C.

7. The method according to claim 1, wherein fatty acid diamide mixtures where the saturated fatty acid bound in the fatty acid diamides constitute less than 15 wt % of the total fatty acid content are used as the fatty acid diamide starting material for oxidative ozonolysis.

8. The method according to claim 7, wherein the yield of diamidic dicarboxylic acid in the oxidative ozonolysis is at least 72 wt % of the theoretical yield.

9. The method according to claim 1, wherein the starting amount by weight of the recrystallization solvent is two to fifteen times the amount by weight of the reaction end product of oxidative ozonolysis minus the amount by weight of the reaction solvent present in the reaction end product.

10. The method according to claim 1, wherein the crystallization solution in steps a) and b) is adjusted so that crystallization takes place from a solution that is saturated at approximately 80° C. to 100° C., and the solution is cooled to a temperature below 25° C.

11. The method of claim 10, wherein the wash solvent residues are removed by distillation.

12. The method according to claim 1, wherein following process step c1) and omitting steps c2) and c3) the diamidic dicarboxylic acids thus obtained are reacted with diamines in a reaction solvent to form the ammonium salts of the diamines from which the diamidic dicarboxylic acids are then released in pure form.

13. The method according to claim 1, wherein following process step c3) the diamidic dicarboxylic acids thus obtained are reacted with diamines in a reaction solvent to form the ammonium salts of the diamines from which the diamidic dicarboxylic acids are then released in pure form.

14. The method according to claim 12, wherein the reaction solvent is added in the form of a water-soluble alcohol in a five-fold to ten-fold amount by weight of the total amount by weight of dicarboxylic acid including an approximately stoichiometric amount of diamines and wherein the salt-forming diamine is selected so that lower molecular diamines are used with an increase in chain length of the dicarboxylic acid to promote a selective crystallization of the salts of the dicarboxylic acids by the resulting influence on the solubility of the salt being formed.

15. The method according to claim 14, wherein the diamines and diamidic dicarboxylic acids mixed with the alcohol are heated to the boiling point of the alcohol and if a clear solution is not formed, the solubility of the salt is shifted by adding water until a clear solution is obtained, the pH of the clear solution is adjusted to approximately 7.5 by adding crude diamidic dicarboxylic acid or diamine, and after cooling the solution, the salts of the diamines that crystallize out are isolated.

16. The method according to claim 12, wherein the diamidic dicarboxylic acids are released from the salts of the diamines by adding dilute mineral acids.

* * * * *